Figure 3:
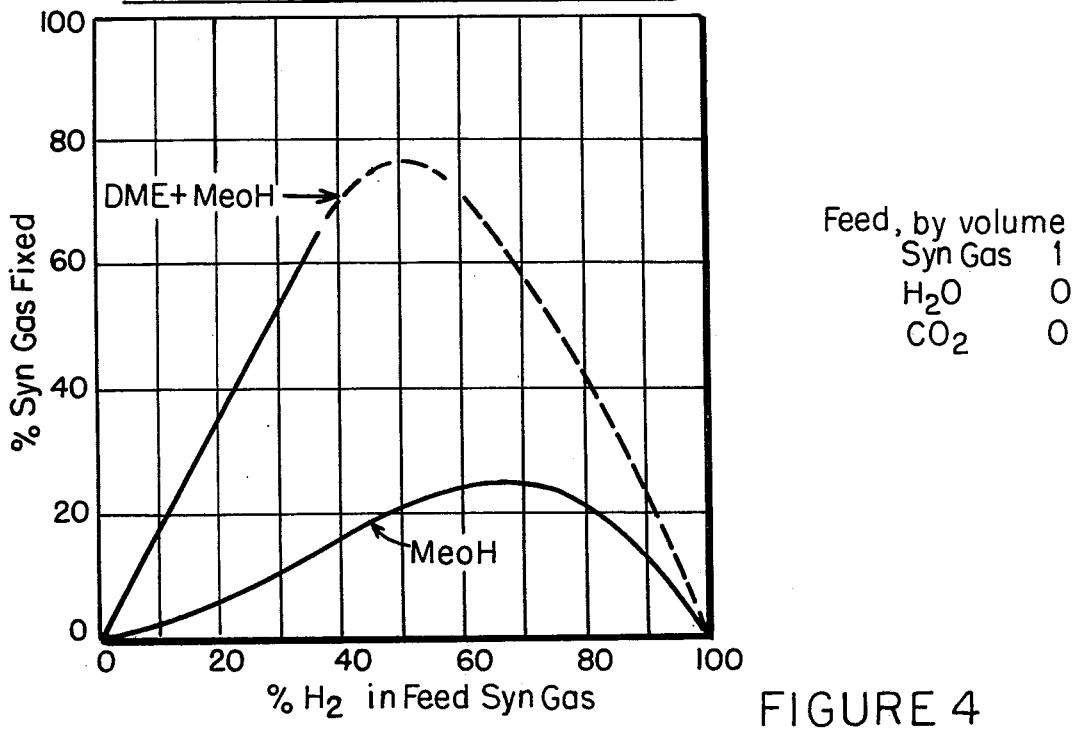
Figure 4:
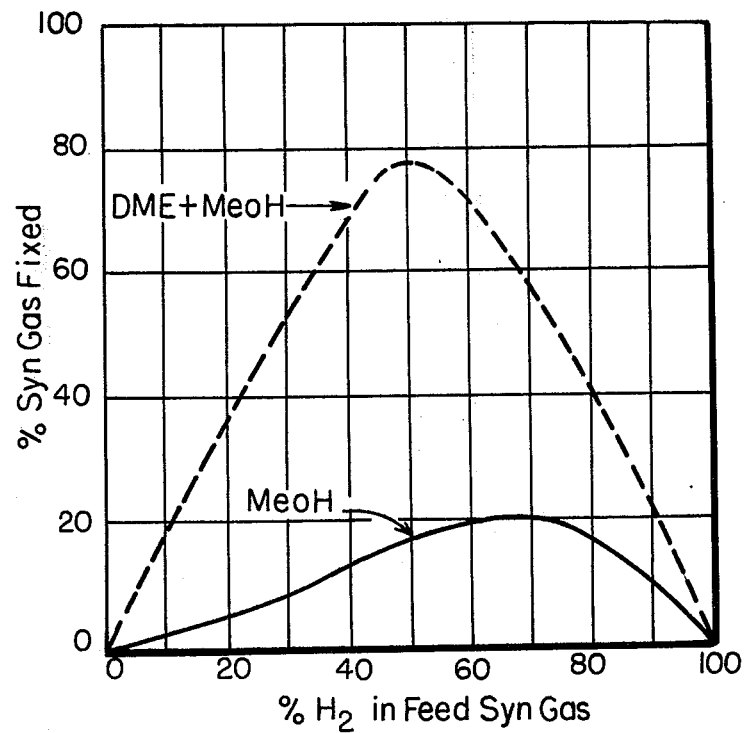
Figure 5:
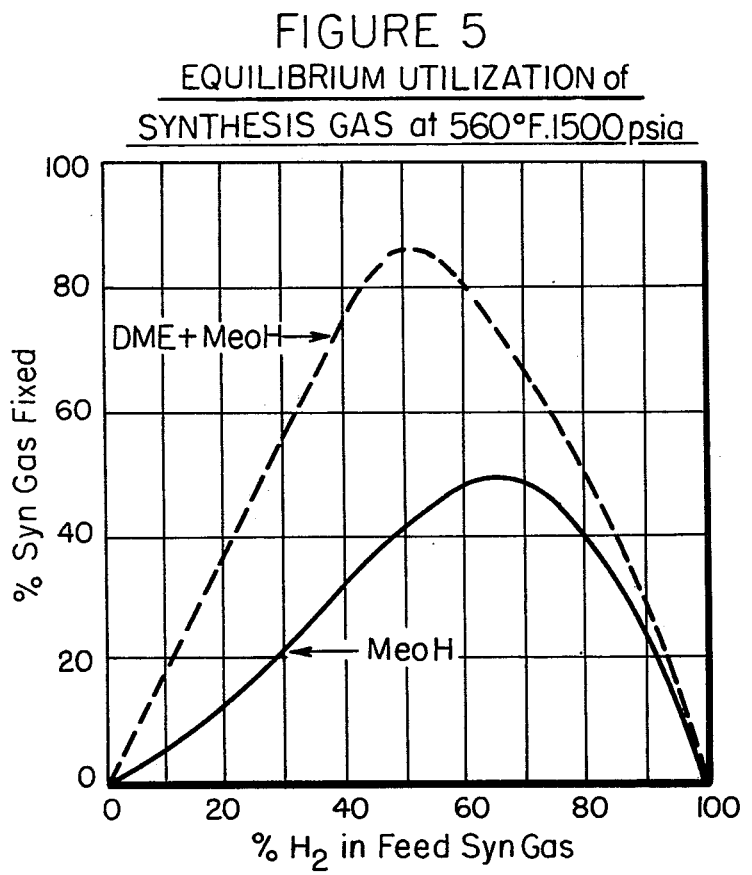
Figure 6:
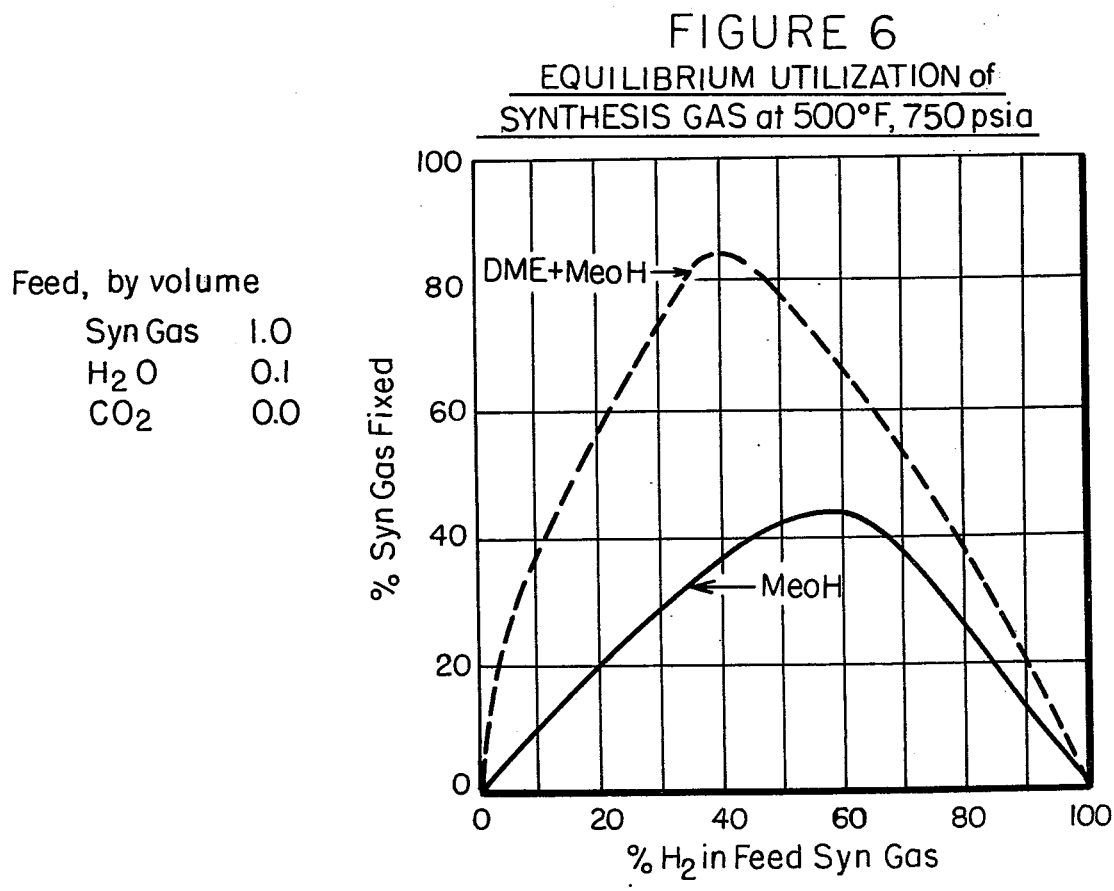

United States Patent [19]

Zahner

[11] 4,011,275

[45] Mar. 8, 1977

[54] CONVERSION OF MODIFIED SYNTHESIS GAS TO OXYGENATED ORGANIC CHEMICALS

[75] Inventor: John C. Zahner, Princeton, N.J.

[73] Assignee: Mobil Oil Corporation, New York, N.Y.

[22] Filed: Aug. 23, 1974

[21] Appl. No.: 499,869

[52] U.S. Cl. .................... 260/668 R; 260/449.5
[51] Int. Cl.² ........................ C07C 15/02
[58] Field of Search ............ 260/668 R, 682, 676, 260/671, 677, 672 T, 668 A, 449.5; 208/135, 141, 118, 120

[56] References Cited

UNITED STATES PATENTS

| | | | |
|---|---|---|---|
| 1,917,323 | 7/1933 | Pier et al. | 260/449.5 |
| 2,964,551 | 12/1960 | Woolcock | 260/449.5 |
| 3,140,322 | 7/1964 | Frilette et al. | 260/648 F |
| 3,728,408 | 4/1973 | Tobias | 260/668 C |
| 3,856,873 | 12/1974 | Burress | 260/672 T |
| 3,894,102 | 6/1975 | Chang et al. | 260/668 R |
| 3,894,107 | 7/1975 | Butter et al. | 260/673 |

OTHER PUBLICATIONS

Brown et al., Ind. Eng. Chem. 21(4), 310–314 (1929).
Natta, Catalysis III, Chap. 8, 349, 372, 374 (1955).

*Primary Examiner*—D. Horwitz
*Attorney, Agent, or Firm*—C. A. Huggett; M. G. Gilman

[57] ABSTRACT

Conversion of synthesis gas (a mixture of carbon monoxide and hydrogen) having a smaller hydrogen to carbon monoxide ratio than that required for methanol stoichiometry, i.e. 2 to 1, by passing such over a zinc-chromium-acid or copper-zinc alumina-acid modified methanol synthesis catalyst under conditions conducive to converting the synthesis gas to a mixture of methanol and dimethyl ether as the desirable organic products.

9 Claims, 8 Drawing Figures

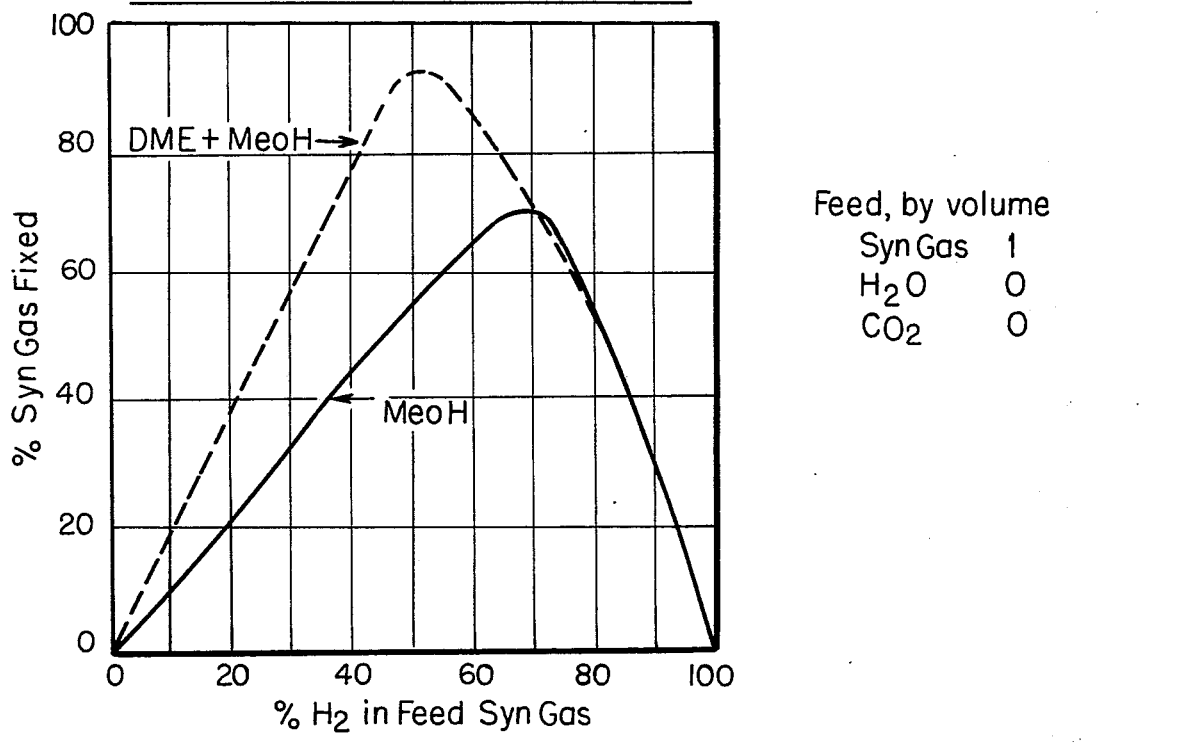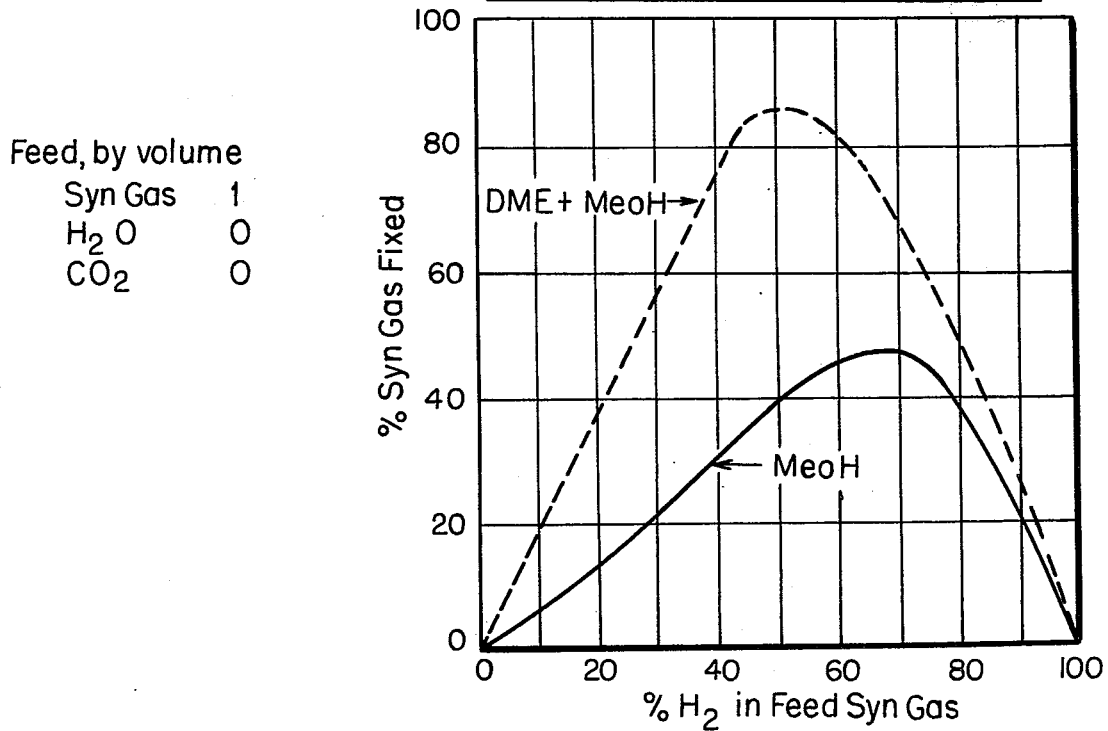

EQUILIBRIUM UTILIZATION of SYNTHESIS GAS at 560°F. 750 psia

EQUILIBRIUM UTILIZATION of SYNTHESIS GAS at 500°F. 325 psia

EQUILIBRIUM UTILIZATION of
SYNTHESIS GAS at 560°F, 1500 psia

EQUILIBRIUM UTILIZATION of
SYNTHESIS GAS at 500°F, 750 psia

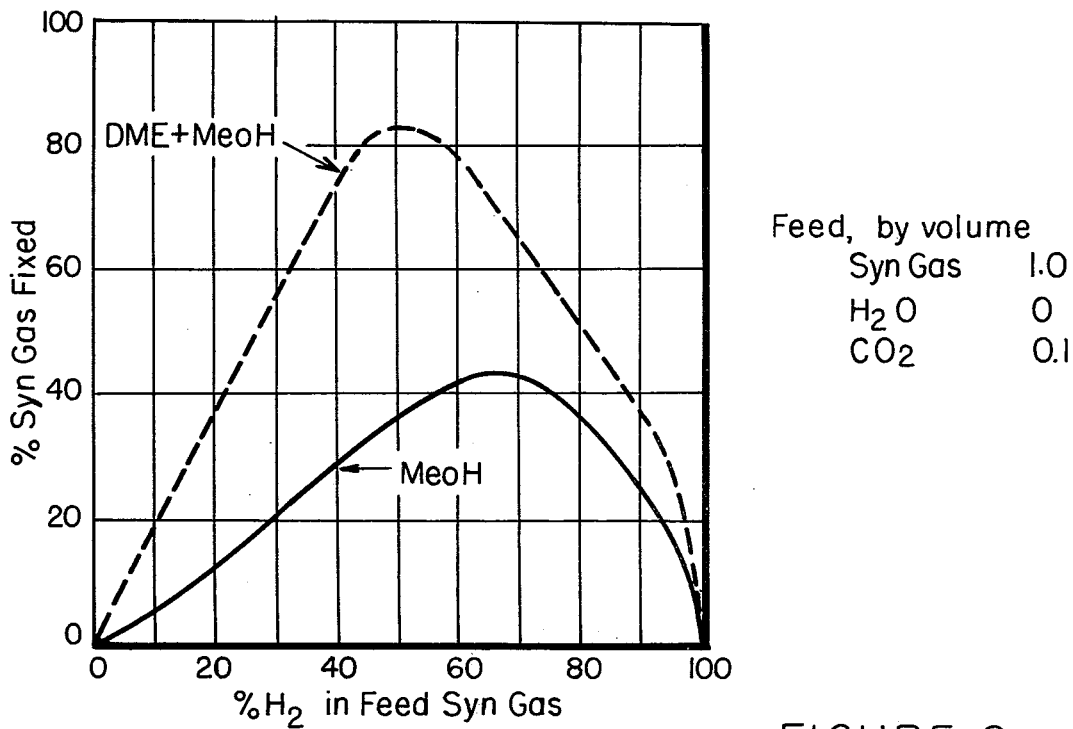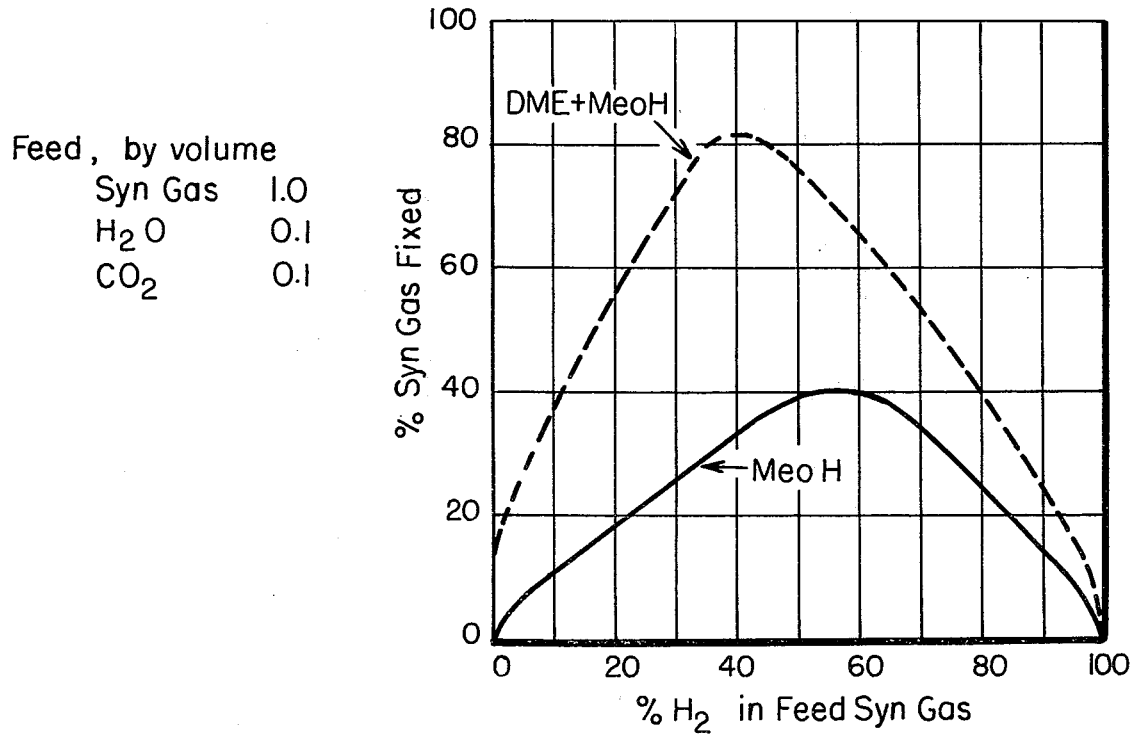

CONVERSION OF MODIFIED SYNTHESIS GAS TO OXYGENATED ORGANIC CHEMICALS

This invention relates to the conversion of carbon monoxide to organic products. It more particularly refers to this conversion to a product of mixed organic compounds having an overall higher carbon to oxygen ratio in the organic portion of the product than in conventional processes.

It is presently known to convert synthesis gas to methanol over various commercially available, so-called methanol synthesis catalysts. Generally speaking, this process requires that the stoichiometry of the synthesis gas be adjusted so that there are about two moles of hydrogen per mole of carbon monoxide. This synthesis gas is then passed into effective contact with a suitable methanol synthesis catalyst whereby a portion of the synthesis gas is converted to methanol. It is conventional to operate this process at considerably elevated temperatures and pressures and with relatively low conversions per pass. Operating in this manner, while having been found to be quite excellent for methanol production, is relatively expensive in terms of capital cost. Equipment must be designed rather large to accomodate the high recycle rate and to withstand the pressures.

In the past, it has usually been desired to produce a product in which the methanol was substantially the only organic compound while minimizing other reaction products as much as possible. For some applications, it may be acceptable and even desirable to carry out this reaction in such a manner as to produce organic compounds other than and in addition to methanol.

It is therefore an object of this invention to provide a modified methanol synthesis process.

It is another object of this invention to provide a modified methanol synthesis process which produces other organic compounds in addition to methanol.

Other and additional objects of this invention will become apparent from a consideration of this entire specification including the claims hereof.

In accord with and fulfilling these objects, one aspect of this invention resides in a process comprising forming a mixture of carbon monoxide and hydrogen having a mole ratio of hydrogen to carbon monoxide of about 0.8 to 1.7, that is, having a molar deficiency of hydrogen of about 15 to 40% when considered from a methanol stoichiometry point of view. The hydrogen deficient synthesis gas is contacted with a modified methanol synthesis catalyst, which modification is in the fact that a minor amound of solid acid function is incorporated with traditional methanol synthesis components, at relatively conventional methanol synthesis reaction conditions. The product produced thereby is a mixture of methanol, dimethyl ether, carbon dioxide and unreacted synthesis gas. Suitable reaction parameters include about 400° to 750° F, about 500 to 4,000 psig and about 10,000 $hv^{-1}$ to 40,000 $hv^{-1}$ space velocity. The catalyst is heterogeneous, it being a solid at reaction conditions, which may be made up of mixtures of Group IB, IIB, and/or VI metal oxides with alumina or other solid acidic materials. Suitable metals are zinc and chromium. Other known metals which are useful in combination in methanol synthesis are copper, manganese and vanadium. It is within the province of this invention to operate the process hereof so as to take a conversion per pass of about 10 to 60%. The process hereof may, and usually does, produce carbon dioxide by-product.

While not wishing to be bound by any particular theory of operations, it appears that when operating the methanol synthesis process as aforesaid with the added acidic catalyst component, there is a reaction product drain in that dimethyl ether appears in the product at the expense of stoichiometric proportions of methanol. A nominal by-product of ether production appears to be water which may undergo an internal water gas shift reaction with carbon monoxide in the synthesis gas reactant whereby producing more hydrogen which is converted to organic compound product.

It is interesting to note that the synthesis gas conversion efficiency is significantly greater in the conversion process hereof using the modified catalyst and modified feed ratios hereof than in prior art methanol synthesis processes. In this regard, reference is here made to the accompanying drawing which is a series of self-explanatory curve pairs relating synthesis gas conversion efficiency, as precent of the synthesis gas fixed into organic products, to proportion of hydrogen in the synthesis gas feed at various, indicated combinations of reaction conditions. In each curve pair figure, it should be noted that reducing the hydrogen content of the synthesis gas coupled with utilizing an otherwise identical catalyst except for the presence or absence of an acidic component as aforesaid has significantly increased the proportion of synthesis gas converted to organic products and that the conversion according to the process of this invention appears to be relatively less sensitive to variations in operating parameters, such as temperature and pressure, than is the prior art process. In these depicted comparisons, the lower curves represent operating a methanol synthesis process under the conditions recited using a copper-zinc heterogeneous catalyst containing 60% copper oxide and 25% zinc oxide. The upper curves represent operating a methanol synthesis process under the conditions recited (which were identical to those of the lower curve) using an identical copper-zinc solid catalyst which had 10% of gamma alumina based upon the total catalyst weight, incorporated therewith.

It is an important aspect of this invention to further convert the product produced by the synthesis gas conversion detailed above. This product is suitably a mixture of methanol, dimethyl ether, perhaps some higher alcohols and/or ethers, perhaps some other oxygenates, carbon dioxide and unconverted carbon monoxide and hydrogen. A relatively simple split of this product, into a heavier (higher boiling) and lighter (lower boiling) fractions, is achieved in a flash type distillation procedure. The raffinate is substantially only organic compounds with perhaps some water; whereas the distillate comprises the carbon oxides, hydrogen and a substantial amount of dimethyl ether.

According to a preferred aspect of this invention, most of the distillate stream is recycled to the synthesis gas conversion zone where it enters into the conversion reaction. Carbon monoxide and hydrogen directly react and carbon dioxide reacts by first going through a hydrogen shift. The dimethyl ether content "goes along for the ride". This recycle improves the overall efficiency of the operation in terms of carbon utilization.

Inerts, such as nitrogen or methane, inevitably accumulate in the recycle stream and must be purged from the system. Therefore, it is most desirable to take some amount of drawdown or purge from the distillate. This drawdown is suitably up to about 25%, preferably about 5 to 15% of the distillate, depending on the amount of inerts present.

An important aspect of this invention, as noted above, is to convert at least the organic portion of this product into other useful materials. In this regard, the raffinate is suitably contacted with a special crystalline aluminosilicate zeolite catalyst so as to convert it to gasoline boiling range, highly aromatic, hydrocarbons and by product water. In this conversion, hydrogen is sometimes produced as a by product. If so, it can be recycled back to the carbon monoxide conversion referred to above if inerts are removed from the hydrogen, in comparable amounts as the inerts are added or generated in the overall system. The hydrogen can be concentrated by refrigeration or other accepted industrial processes. By product water can also be recycled as steam back to a synthesis gas generation step if there is one in the overall process configuration.

It is a desirable modification of this conversion process to admix the aforesaid drawdown stream containing dimethyl ether with the raffinate and to subject this combined stream to conversion to gasoline boiling range hydrocarbons. It is also desirable to subject the product of raffinate conversion to distillation in order to separate the $C_5+$ normally liquid, portion from the remainder of the product. This remainder overhead may be processed to make more gasoline, LPG, fuel gases pipeline gas as desired in a given processing location and environment.

The latter referred to conversion is not considered to be per se inventive here, it being the subject of other patent applications copending herewith. This conversion is carried out at least about 500° F, preferably about 550° F to 850° F in the effective presence of a special zeolite catalyst. Suitable space velocities are about 0.1 to 100 LHSV. Pressures may be up to about 50 atmospheres.

The class of zeolites utilized in this invention has some unusual properties. These zeolites by themselves induce profound transformations of aliphatic hydrocarbons to aromatic hydrocarbons in commercially desirable yields. Although they have unusually low alumina contents, i.e. high silica to alumina ratios, they are very active even when the silica to alumina ratio exceeds 30. The activity is surprising since the alumina in the zeolite framework is believed responsible for catalytic activity. They retain their crystallinity for long periods in spite of the presence of steam at high temperature which induces irreversible collapse of the framework of other zeolites, e.g. of the X and A type. Furthermore, carbonaceous deposits, when formed, may be removed by burning at higher than usual temperatures to restore activity.

An important characteristic of the crystal structure of this class of zeolites is that it provides constrained access to, and egress from, this intracrystalline free space by virtue of having a pore dimension greater than about 5 Angstroms and pore windows of about a size such as would be provided by 10-membered rings of oxygen atoms. It is to be understood, of course, that these rings are those formed by the regular disposition of the tetrahedra making up the anionic framework of the crystalline aluminosilicate, the oxygen atoms themselves being bonded to the silicon or aluminum atoms at the centers of the tetrahedra. Briefly, the preferred zeolites useful in this invention possess, in combination: a silica to alumina ratio of at least about 12; and a structure providing constrained access to the crystalline free space.

The silica to alumina ratio referred to may be determined by conventional analysis. This ratio is meant to represent, as closely as possible, the ratio in the rigid anionic framework of the zeolite crystal and to exclude aluminum in the binder or in cationic form within the channels. Although zeolites with a silica to alumina ratio of at least 12 are useful, it is preferred to use zeolites having higher ratios of at least about 30. Such zeolites, after activation, acquire an intracrystalline sorption capacity for normal hexane which is greater than that for water, i.e. they exhibit "hydrophobic" properties. It is believed that this hydrophobic character is advantageous in the present invention.

The type zeolites useful in this invention freely sorb normal hexane and have a pore dimension greater than about 5 Angstroms. In addition, the structure must provide constrained access to larger molecules. It is sometimes possible to judge from a known crystal structure whether such constrained access exists. For example, if the only pore windows in a crystal are formed by eight membered rings of oxygen atoms, the access to molecules of larger cross-section than normal hexane is excluded and the zeolite is not of the desired type. Windows of ten-membered rings are preferred, although excessive puckering or pore blockage may render these zeolites ineffective. Twelve-membered rings do not generally appear to offer sufficient constraint to produce the advantageous conversions, although structures can be conceived, due to pore blockage or other cause, that may be operative.

Rather than attempt to judge from crystal structure whether or not a zeolite possesses the necessary constrained access, a simle determination of the "constraint index" may be made by passing continuously a mixture of equal weight of normal hexane and 3-methylpentane over a small sample, approximately 1 gram or less, of zeolite at atmospheric pressure according to the following procedure. A sample of the zeolite, in the form of pellets or extrudate, is crushed to a particle size about that of coarse sand and mounted in a glass tube. Prior to testing, the zeolite is treated with a stream of air at 1000° F for at leat 15 minutes. The zeolite is then flushed with helium and the temperature adjusted between 550° F and 950° F to give an overall conversion between 10% and 60%. The mixture of hydrocarbons is passed at 1 liquid hourly space velocity (i.e. 1volume of hydrocarbon per volume of zeolite per hour) over the zeolite with a helium dilution to give a helium to total hydrocarbon mole ratio of 4:1. After 20 minutes on stream, a sample of the effluent is taken and analyzed, most conveniently by gas chromatogrophy, to determine the fraction remaining unchanged for each of the two hydrocarbons.

The "constraint index" is calculated as follows:

Constraint Index =

$$\frac{\log_{10} \text{(fraction of n-hexane remaining)}}{\log_{10} \text{(fraction of 3-methylpentane remaining)}}$$

The constraint index approximates the ratio of the cracking rate constants for the two hydrocarbons. Zeolites suitable for use as catalyst for the present invention are those having a constraint index from 1.0 to 12.0, preferably 2.0 to 7.0.

The class of zeolites defined herein is exemplified by ZSM-5, ZSM-11, ZSM-12, ZSM-21, TEA mordenite and other similar materials. Recently issued U.S. Pat. No. 3,702,886 describing and claiming ZSM-5 is incorporated herein by reference.

ZSM-11 is more particularly described in U.S. Pat. No. 3,709,979, the entire contents of which are incorporated herein by reference.

ZSM-12 is more particularly described in West German Offenlagunschrifft No. 2,213,109, the entire contents of which are incorporated herein by reference.

ZSM-21 is more particularly described in U.S. Application, Ser. No. 358,192, filed May 7, 1973, the entire contents of which are incorporated herein by reference.

TEA mordenite is more particularly described in U.S. Application Ser. No. 130,442 filed Apr. 11, 1971, the entire contents of which are incorporated herein by reference.

The specific zeolites described, when prepared in the presence of organic cations, are catalytically inactive, possibly because the intracrystalline free space is occupied by organic cations from forming solution. They may be activated by heating in an inert atmosphere at 1000° F for one hour, for example, followed by base exchange with ammonium salts followed by calcination at 1000° F in air. The presence of organic cations in the forming solution may not be absolutely essential to the formation of this type zeolite; however, the presence of these cations does appear to favor the formation of this special type of zeolite. More generally, it is desirable to activate this type zeolite by base exchange with ammonium salts followed by calcination in air at about 1000° F for from about 15 minutes to about 24 hours.

Natural zeolites may sometimes be converted to this type zeolite by various activation procedures and other treatments such as base exchange, steaming, alumina extraction and calcination, in combinations. Natural minerals which may be so treated include ferrierite, brewsterite, stillbite, dachiardite, epistilbite, heulandite and clinoptilolite. The preferred crystalline aluminosilicates are ZSM-5, ZSM-11, ZSM-12, ZSM-21 and TEA mordenite, with ZSM-5 particularly preferred.

In a preferred aspect, the zeolites used herein are selected as those having a crystal density, in the dry hydrogen form, of not substantially below about 1.6 grams per cubic centimeter. It has been found that zeolites which satisfy all three of these criteria are most desired. Therefore, the preferred catalysts of this invention utilize zeolites having a constraint index as defined above of about 1 to 12, a silica to alumina ratio of at least about 12 and a dried crystal density of not less than about 1.6 grams per cubic centimeter. The dry density for known structures may be calculated from the number of silicon plus aluminum atoms per 1000 cubic Angstroms, as given, e.g. on page 11 of the article on Zeolite Structure by W. M. Meier. This paper, the entire contents of which are incorporated herein by reference, is included in "Proceedings of the Conference on Molecular Sieves, London, April 1967", published by the Society of Chemical Industry, London, 1968. When the crystal structure is unknown, the crystal framework density may be determined by classical pyknometer techniques. For example, it may be determined by immersing the dry hydrogen form of the zeolite in an organic solvent which is not sorbed by the crystal. It is possible that the unusual sustained activity and stability of this class of zeolites is associated with its high crystal anionic framework density of not less than about 1.6 grams per cubic centimeter. This high density of course must be associated with a relatively small amount of free space within the crystal, which might be expected to result in more stable structures. This free space, however, is important as the locus of catalytic activity.

What is claimed is:

1. In the process of converting synthesis gas to gasoline boiling range hydrocarbons by the sequential steps of converting said synthesis gas to a product comprising predominantly methanol and then converting at least the methanol portion of this product to gasoline boiling range hydrocarbons by contact thereof with a crystalline aluminosilicate zeolite having a silica to alumina ratio of at least about 12, a constraint index of 1 to 12 and a crystal density of not substantially below about 1.6 grams per cubic centimeter, at a temperature of at least about 500° F; the improvement, whereby increasing the proportion of synthesis gas converted to said product comprising predominantly methanol and dimethyl ether available for conversion to gasoline boiling range hydrocarbons by contact with said zeolite, which comprises adjusting the hydrogen-carbon monoxide mole ratio in said synthesis gas to about 0.8 to 1.7, which is a hydrogen deficiency with respect to methanol stoichiometry; converting said hydrogen deficient synthesis gas, at elevated pressures of about 500 to 4000 psig, space velocity of about 10,000 $hv^{-1}$ to 40,000 $hv^{-1}$ and temperatures of about 400 to 570° F in contact with a solid metallic methanol synthesis catalyst having a solid acid component incorporated therewith, to a product comprising a high ratio of dimethyl ether to methanol and representing a high conversion of synthesis gas thereto; and converting at least said dimethyl ether and methanol to gasoline boiling range hydrocarbons as aforesaid.

2. The improved process claimed in claim 1 wherein said feed synthesis gas has a hydrogen to carbon monoxide ratio of about 1.5.

3. The improved process claimed in claim 1 wherein said methanol synthesis catalyst comprises a copper oxide-zinc oxide on alumina catalyst.

4. The improved process claimed in claim 1 wherein said methanol synthesis catalyst comprises a zinc-chromium oxide catalyst.

5. The improved process claimed in claim 1 wherein the acid component comprises about 1 to 25% of the methanol synthesis catalyst.

6. The improved process claimed in claim 1 wherein said zeolite is ZSM-5.

7. The improved process claimed in claim 1 including resolving the product of said synthesis gas conversion into an organic compound rich raffinate and an organic compound containing distillate; drawing down a portion of said distillate; and converting each of said drawdown and raffinate over said zeolite.

8. The improved process claimed in claim 7 including recycling at least a portion of the non-drawdown distillate into admixture with fresh synthesis gas prior to contacting said catalyst.

9. The improved process claimed in claim 7 including mixing said drawdown and said raffinate; and converting said mixture over said zeolite.

* * * * *